(12) United States Patent
Kelly et al.

(10) Patent No.: US 7,097,887 B2
(45) Date of Patent: Aug. 29, 2006

(54) LIQUID CRYSTAL COMPOUNDS

(75) Inventors: Stephen M Kelly, Hull (GB); Neil L Campbell, Teddington (GB); Warren L Duffy, Southampton (GB)

(73) Assignee: QinetiQ Limited, London (GB)

( * ) Notice: Subject to any disclaimer, the term of this patent is extended or adjusted under 35 U.S.C. 154(b) by 0 days.

(21) Appl. No.: 10/483,403

(22) PCT Filed: Jul. 10, 2002

(86) PCT No.: PCT/GB02/03165

§ 371 (c)(1), (2), (4) Date: Mar. 31, 2004

(87) PCT Pub. No.: WO03/006574

PCT Pub. Date: Jan. 23, 2003

(65) Prior Publication Data

US 2004/0149957 A1    Aug. 5, 2004

(30) Foreign Application Priority Data

Jul. 12, 2001    (GB) .................................. 0116991.1

(51) Int. Cl.
*C09K 19/30* (2006.01)
*C09K 19/34* (2006.01)
*C07D 319/06* (2006.01)
*C07D 407/04* (2006.01)
*C07D 407/06* (2006.01)

(52) U.S. Cl. ................ 428/1.1; 252/299.5; 252/299.61; 252/299.63; 549/370; 549/374; 549/369

(58) Field of Classification Search ............ 252/299.01, 252/299.5, 299.61, 299.63; 428/1.1; 549/369, 549/370, 374
See application file for complete search history.

(56) References Cited

U.S. PATENT DOCUMENTS

| 4,830,469 A | 5/1989 | Breddels et al. |
| 5,746,940 A | 5/1998 | Coates et al. |

FOREIGN PATENT DOCUMENTS

| EP | 0 132 553 A | 2/1985 |
| EP | 0 315 050 A | 5/1989 |
| EP | 0 385 471 A | 9/1990 |
| EP | 0824141 A1 | 2/1998 |
| JP | 64-22835 | * 1/1989 |
| WO | 87/07266 A | 12/1987 |
| WO | 90/04622 A | 5/1990 |
| WO | 93/02152 A | 2/1993 |
| WO | 95/27920 | 10/1995 |

OTHER PUBLICATIONS

Chemical Abstracts 111:15492 and JP 01022835 A2 (Dainippon), see abstract and compound with Registry No. 121191-21-7. (Jan. 25, 1989).
Kelly; "The Synthesis and Liquid Crystal Transition Temperatures of Some Weakly Polar Nematic Trans-4-Substituted-Cyclohexyl (E)-Alk-2-Enoates"; Liquid Crystals, Taylor and Francis Ltd., London, GB, vol. 17, No. 2, Aug. 1, 1994, pp. 211-255, XP000460892.
Schadt et al; "Material Properties, Structural Relations With Molecular Ensembles and Electro-Optical Performance of New Bicyclohexane Liquid Crystals in Field-Effect Liquid Crystal Displays"; Liquid Crystals, Basingstoke, Hampshire, GB, vol. 5, No. 1, 1989, pp. 293-312, XP000210415.
Patent Abstracts of Japan vol. 015, No. 392, Oct. 04, 1991 & JP 03 161453 A, Jul. 11, 1991.

* cited by examiner

*Primary Examiner*—Shean C. Wu
(74) *Attorney, Agent, or Firm*—Nixon & Vanderhye P.C.

(57) ABSTRACT

The use of a compound of formula (I)

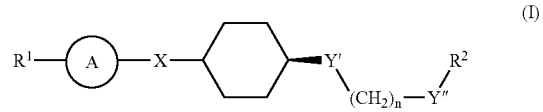

Figure 1:
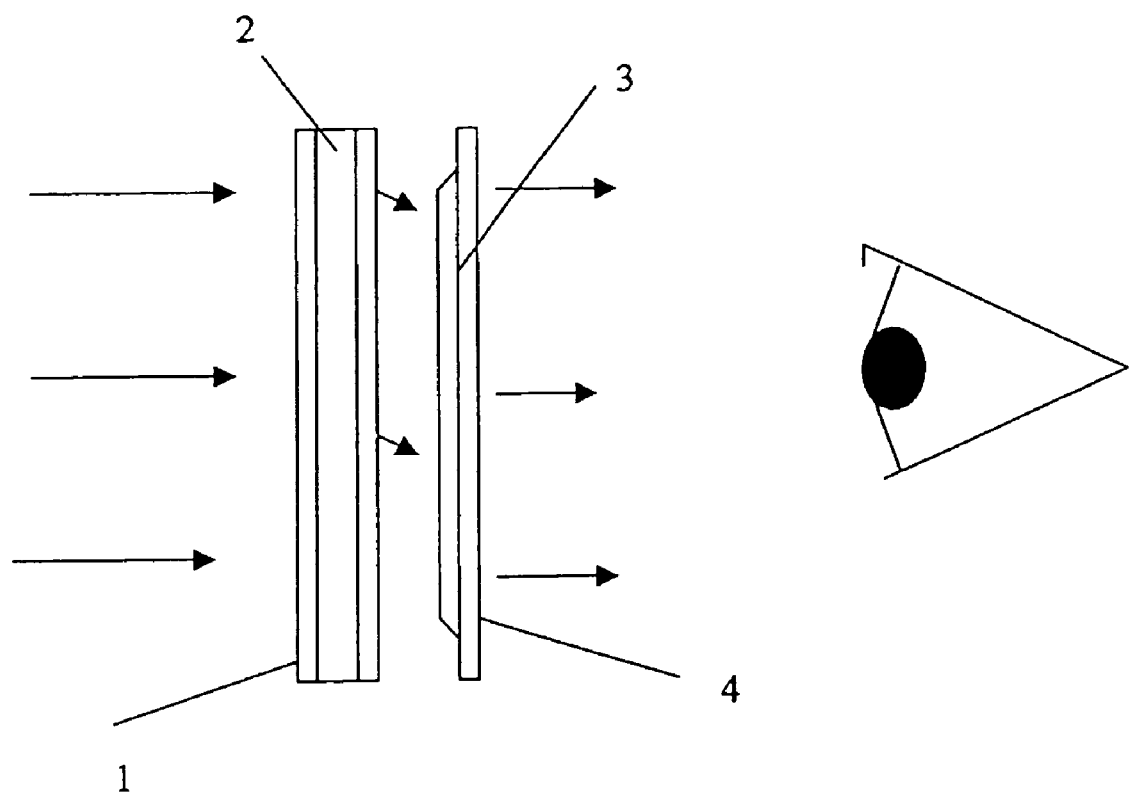

wherein $R^1$ is an alkyl or alkenyl group, either of which may be optionally interposed with one or more oxygen or sulphur atoms, $R^2$ is an alkyl or alkenyl group, Y' and Y" are independently selected from oxygen or sulphur, n is an integer from 1 to 5, X is a direct bond or a $C_{1-4}$alkylene or $C_{2-4}$alkenylene chain, and A is group comprising one or two rings which are independently selected from aryl, heterocylic or cycloalkyl rings, and when there are two rings, they are bonded together directly or by way of a $C_{1-4}$alkylene or $C_{2-4}$alkenylene group, for increasing the u.v. stability of a liquid crystal mixture.

The compounds of formula (I) are u.v. stable and are useful in liquid crystal devices which are exposed to high levels of u.v. light such as phosphor display cells.

Certain compounds are novel and these form a further aspect of the invention.

19 Claims, 1 Drawing Sheet

LIQUID CRYSTAL COMPOUNDS

This application is the U.S. national phase of international application PCT/GB02/03165 filed in English on 10 Jul. 2002, which designated the U.S. PCT/GB02/03165 claims priority to GB Application No. 0116991.1 filed 12 Jul. 2001. The entire contents of these applications are incorporated herein by reference.

The present invention relates to liquid crystal mixtures which are stable to u.v. light, to liquid crystal devices containing these and to methods for increasing the u.v. stability of liquid crystal mixtures. Certain compounds useful in these mixtures are novel and these, together with processes for their preparation, form a further aspect of the invention.

The term "liquid crystals" is well known. It refers to compounds which, as a result of their structure, will align themselves in a similar orientation, preferably at working temperatures, for example of from −40 to 200° C. These materials are useful in various devices, in particular the liquid crystal display devices or LCDs. Liquid crystals can exist in various phases. In essence there are three different classes of liquid crystalline material, each possessing a characteristic molecular arrangement. These classes are nematic, chiral nematic (cholesteric) and smectic.

Broadly speaking, the molecules of nematic compounds will align themselves in a particular orientation in a bulk material. Smectic materials, in addition to being orientated in a similar way, will align themselves closely in layers.

A wide range of smectic phases exists, for example smectic A and smectic C. In the former, the molecules are aligned perpendicularly to a base or support, whilst in the latter, molecules may be inclined to the support. Some liquid crystal materials possess a number of liquid crystal phases on varying the temperature. Others have just one phase. For example, a liquid crystal material may show the following phases on being cooled from the isotropic phase:-isotropic-nematic-smectic A-smectic C-solid. If a material is described as being smectic A then it means that the material possesses a smectic A phase over a useful working temperature range.

Such materials are useful, in particular in display devices where their ability to align themselves and to change their alignment under the influence of voltage, is used to impact on the path of polarised light, thus giving rise to liquid crystal displays. These are widely used in devices such as watches, calculators, display boards or hoardings, computer screens, in particular laptop computer screens etc. The properties of the compounds which impact on the speed with which the compounds respond to voltage charges include molecule size, viscosity ($\Delta n$), dipole moments ($\Delta \epsilon$), conductivity etc.

In some cases however, the devices are subject to high levels of radiation such as ultra-violet radiation. Many liquid crystal compounds are not stable under these circumstances and can deteriorate rapidly.

Some examples of alkylene glycol liquid crystal compounds are found in EP-A-0385471 and JP-64-22835. EP-A-0824141 describes a complex series of liquid crystal mixtures, some of which may contain alkylene glycol compounds.

The applicants have found that certain of these structural types, as well as having useful liquid crystal properties, also have particularly good resistance to u.v. light, and so may be used to enhance the u.v. stability of liquid crystal mixtures.

The present invention provides the use of a compound of formula (1)

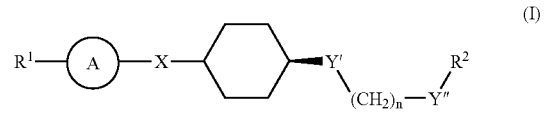

wherein $R^1$ is an alkyl or alkenyl group, either of which may be optionally interposed with one or more oxygen or sulphur atoms, $R^2$ is an alkyl or alkenyl group, Y' and Y" are independently selected from oxygen or sulphur, n is an integer from 1 to 5, X is a direct bond or a $C_{1-4}$alkylene or $C_{2-4}$alkenylene chain, and A is group comprising one or two rings which are independently selected from aryl, heterocylic or cycloalkyl rings, and when there are two rings, they are bonded together directly or by way of a $C_{1-4}$alkylene or $C_{2-4}$alkenylene group, for increasing the u.v. stability of a liquid crystal mixture.

As used herein the term "alkyl" refers to straight or branched chain alkyl groups, suitably containing up to 20, more suitably up to 10 and preferably up to 6 carbon atoms. The term "alkylene" refers to alkyl groups which are divalent and "cycloalkyl" refers to alkyl groups which have at least 3 carbon atoms, and which are cyclic in structure. The term "alkenyl" refers to straight or branched unsaturated chains having from 2 to 20 and preferably from 2 to 10 carbon atoms. The term "aryl" refers to aromatic rings such as phenyl and naphthyl, but preferably phenyl.

References to "heterocyclic groups" refer to rings, which suitably contain from 4 to 8 atoms, up to three of which are heteroatoms selected from oxygen, nitrogen or sulphur. They may be saturated or unsaturated, but are preferably saturated.

Suitably, rings in group A are para substituted, and where they are saturated, substituents are preferably in a trans relationship to each other. Particularly preferred examples of group A in formula (I) are groups of formula (i), (ii), (iii), (iv) or (v)

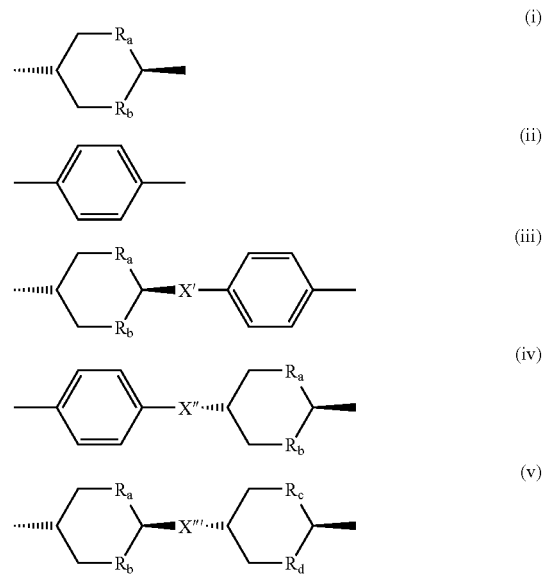

where X', X" and X''' are each selected from a direct bond, a $C_{1-4}$alkylene chain or a $C_{2-4}$alkenylene chain, and each group $R_a$, $R_b$, $R_c$ and $R_d$ are independently selected from $CH_2$ or oxygen. In particular where one of $R_a$ or $R_b$, or $R_c$ or $R_d$ is oxygen, the other is also oxygen so that the group A is or includes a dioxane ring.

In particular however, $R_a$, $R_b$, $R_c$ and $R_d$, where present, are $CH_2$ groups.

Suitably Y' and Y" are oxygen.

In a particularly preferred embodiment, n is 2.

Suitably $R^2$ is a $C_{1-10}$alkyl, preferably $C_{1-6}$alkyl and most preferably $C_{1-3}$alkyl. Alternatively, $R^2$ is alkyl having at least 5 carbon atoms, for example from 5 to 10 carbon atoms.

Preferably, X is a direct bond or a $C_{1-2}$alkylene chain, and most preferably X is a direct bond.

Where X is a $C_{2-4}$alkenylene chain, it is suitably a group of sub-formula (x), (xi) or (xii)

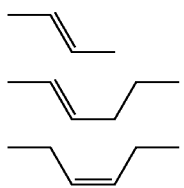

The cyclohexyl ring illustrated in FIG. 1 is suitably in the trans configuration. Thus, in particular, the compound of formula (I) is suitably a compound of formula (IA)

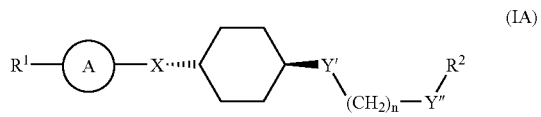

where $R^1$, $R^2$, A, X, Y', Y" and n are as defined above.

In a preferred embodiment, $R^1$ is a straight chain $C_{1-6}$alkyl group and most preferably a $C_{3-5}$alkyl group, which optionally contains one or two oxygen or sulphur atoms. For example, a particular example of a group $R^1$ is a group of formula (II)

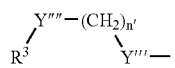

where n' is an integer from 1 to 5, Y''' and Y'''' are independently selected from oxygen or sulphur and $R^3$ is alkyl, in particular $C_{1-4}$alkyl. Preferably n' is 2. Preferably Y''' and Y'''' are oxygen.

Other particular examples of groups $R^1$ are $C_{3-5}$alkyl.

Yet further examples are $C_{8-20}$alkyl.

In an alternative embodiment, $R^1$ is an alkenyl group and in particular a $C_{2-10}$alkenyl group. Suitably the alkenyl group contains two or more double bonds, and is preferably a diene of formula (VI)

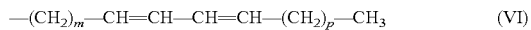

where m and p are 0 or an integer from 1–5, provided that m+p does not exceed 5. Preferably m and p are 0.

Particularly suitable rings A in formula (I) are groups of sub-formula (i), (iii) and (v), and preferred rings A are groups of sub-formula (i). In groups of sub-formula (iii), (iv)

and (v), X', X" and X''' are suitably direct bonds or $C_{1-2}$alkylene groups. Particularly, these are direct bonds. Where these are $C_{2-4}$alkenylene groups, these are suitably selected from groups (x), (xi) and (xii) as listed above in relation to X.

Thus particular examples of compounds of formula (I) are compounds of formula (III)

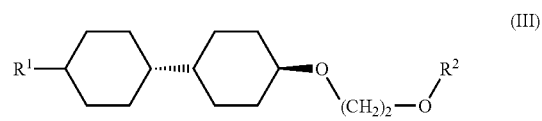

where $R^1$ and $R^2$ are as defined above.

Particular examples of compounds of formula (III) are set out in Table 1.

TABLE 1

| Compound No. | $R^1$ | $R^2$ |
|---|---|---|
| 1 | $C_3H_7$ | $CH_3$ |
| 2 | $C_5H_{11}$ | $CH_3$ |
| 3 | $C_3H_7$ | $C_2H_5$ |
| 4 | $C_5H_{11}$ | $C_2H_5$ |
| 5 | $C_3H_5$ | $C_3H_7$ |

These compounds are suitably added to liquid crystal mixtures in order to increase the u.v. stability of those mixtures. Other components of the mixture will include liquid crystal compounds of various structures as are well known in the art. Suitably the compound of formula (I) is added in sufficient quantities to produce a significant effect on the u.v. stability of the mixture. Therefore, the mixture will suitably contain the compound of formula (I) in an amount of from 5–80%, preferably from 5–40%, and most preferably from 10–30% by weight.

Compounds of formula (I) may be prepared by conventional methods. However, in accordance with an aspect of the invention, they are prepared by reacting a compound of formula (IV)

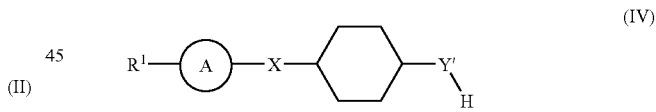

where $R^1$, A, X and Y' are as defined in relation to formula (I); with a compound of formula (V)

where Y" and $R^2$ is as defined in relation to formula (I) and Z is a leaving group. The reaction is suitably effected in an organic solvent such as tetrahydrofuran in the presence of a strong base such as an alkali metal hydride for instance, sodium hydride. Suitable leaving groups Z include halo such as chloro, bromo or iodo, mesylate and tosylate, and in particular are halo groups such as bromo.

Compounds of formula (IV) are either known compounds or they can be prepared from known compounds by conventional methods.

Compounds of formula (I) have liquid crystal properties and in particular are nematic compounds. Thus they may be included in mixtures used in liquid crystal devices including liquid crystal display cells, such as twisted nematic cells (TN) (such as standard TN cells), supertwist nematic cells (STN) and supertwist birefringence effect (SBE) cells.

Such devices form a further aspect of the invention.

The compounds of formula (I) have good stability in the presence of radiation such as ultraviolet radiation. In particular they do not absorb radiation at the wavelengths used in many liquid crystal devices. These properties make them particularly useful, either alone or in mixture with other liquid crystal compounds, in liquid crystalline displays that are exposed to high levels of ultraviolet radiation, such as those used in outdoor displays. In addition, they may be utilized in conjunction with phosphorescent substrates or phosphor layer liquid crystal devices, such as those described in U.S. Pat. No. 4,830,469, WO 95/27920, EP-A-185495 and European Patent No 0755532.

These devices are particularly suitable for display cells and especially colour display cells as they overcome problems associated with the use of liquid crystals as shutters for transmitting light to a viewer. The light scattering or birefringent properties of these compounds is useful in this respect and may be controlled by application of an electrical field. However the liquid crystal material is sensitive to the angle at which light passes through it, and therefore there may be difficulties with viewing angle when these are viewed directly.

These problems are overcome in devices such as those mentioned above, by directing light from a light source, usually an ultraviolet light source, through the liquid crystal layer onto self-radiating elements or phosphors. These are activated by light reaching them through the liquid crystal layer, and thereafter emit light at a desirable viewing angle. Each phosphor therefore can constitute a pixel in a display or a combination of red, blue and green phosphors may be grouped to form a pixel which can emit light at any colour of the spectrum, depending upon the relative stimulation of each.

Thus a preferred liquid crystal device according to the invention is a display cell comprising a layer of a liquid crystal material wherein the liquid crystal material comprises a compound of formula (1), means for addressing the liquid crystal material so as to allow light to pass through it when appropriately addressed, and an emitting layer comprising phosphor elements, arranged to receive light passing through the liquid crystal layer.

Such devices are illustrated schematically in FIG. 1 hereinafter. These devices may be arranged differently depending upon the intended application.

Suitably in these devices, the liquid crystal material is contained between two parallel, spatially separated transparent substrate plates (1), either in individual cells or in a continuous panel. Liquid crystal material (2), such as a compound of the present invention is provided in the cell, and the orientation is controllable by addressing means such as electrodes arranged on either side of the layer (not shown). Light from a light source is supplied in the direction of the arrow, and is either internally reflected by the liquid crystal material, or diverted to phosphors (3) on an emitting layer (4), depending upon the activation of the liquid crystal material. The phosphors may then emit light at a preferred viewing angle.

Devices may also contain polarisers and/or dichroic ultraviolet light absorbers (as described in U.S. Pat. No. 4,830, 469).

A particularly preferred device further comprises means for collimating activating light towards the phosphors. Various arrangements for such collimating means are described in WO 95/27920. They include lenses, which may be arranged in or on one of the layers.

Light from an ultra-violet light source, is supplied to the liquid crystal layer, either directly onto the back or from the edge using for example the transparent backing plate as a light guide. The addressing means control the orientation of the liquid crystal material, within each cell or region of the panel as is well understood in the art. As a result, light may or may not be directed onto a particular phosphor element, which is either activated to emit light or remain dark, respectively. By appropriate control of the addressing means, each pixel point has individual visible light output characteristics at any given point in time.

Such devices may include computer or television screens, and these may contain hundreds of thousands of individual pixels, which control the amount of red, green or blue light reaching a very small area of the screen, for example of 100 μm or less. In such cases, one of the electrodes used to address the liquid crystal material may be connected together in columns, and the other connected in rows (where rows and columns are perpendicular to each other) in order to reduce the number of electrical connections required. However, in order to ensure that pixels are controlled individually, these need to be multiplexed as understood in the art. Multiplexing generally achieved by applying a voltage which cycles between the desired voltage and zero many times per second. As each row receives the required voltage, a positive or negative voltage is applied to each column so that individual pixels within the row are addressed in the required manner. This means that the liquid crystal of all the "on" pixels will subject to a voltage in excess of the threshold voltage for that compound. All rows in the display are scanned to refresh the pixels.

Certain compounds of formula (I) are novel and these form a further aspect of the invention. In particular, the invention further provides a compound of formula (VII)

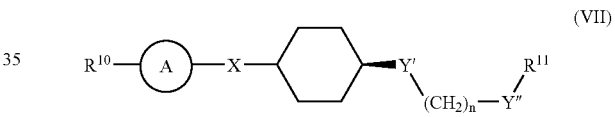

wherein $R^{10}$ is an alkyl or alkenyl group, either of which may be optionally interposed with one or more oxygen or sulphur atoms, $R^{11}$ is an alkyl or alkenyl group, Y', Y", n, X and A are as defined above in relation to formula (I) provided that when A is cycloalkyl, X is a direct bond or a $C_2$alkylene chain, n is 2, Y' and Y" are both oxygen, $R^{11}$ is methyl, and $R^{10}$ is an alkyl group, it contains more than 3 carbon atoms.

Particular groups of compounds of formula (VII) are compounds of formula (VIIA)

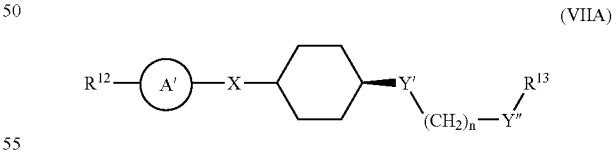

wherein $R^{12}$ is an alkyl or alkenyl group, either of which may be optionally interposed with one or more oxygen or sulphur atoms, $R^{13}$ is an alkyl or alkenyl group, Y', Y''', n, and X, and A is a group comprising one or two rings which are independently selected from aryl or heterocylic, and when there are two rings, they are bonded together directly or by way of a $C_{1-4}$alkylene or $C_{2-4}$alkenylene group.

Preferred examples of $R^{12}$ and $R^{13}$ are as defined above in relation to $R^1$ and $R^2$. Similarly preferred examples of X, Y', Y" and n are as defined above in relation to corresponding variables in formula (I). Preferred examples of A' are groups of sub-formula (ii), (iii), (iv) or (v) as defined above. Alternatively, A' may be a dioxane ring.

An alternative group of compounds of formula (VII) are compounds of formula (VIIB)

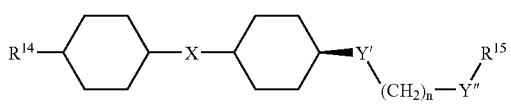

(VIIB)

where X, Y', Y" and n are as defined above in relation to formula (I), $R^{14}$ is an alkyl or alkenyl group, either of which may be optionally interposed with one or more oxygen or sulphur atoms, and $R^{15}$ is an alkyl or alkenyl group, provided that when $R^{15}$ is methyl and $R^{14}$ is alkyl of at least 4 and preferably at least 8 carbon atoms.

Suitably $R^{14}$ is alkenyl.

More suitably $R^{14}$ is alkyl of at least 4 and preferably at least 8 carbon atoms.

Suitably $R^{15}$ is alkenyl

More suitably $R^{15}$ is alkyl of at least 2 and preferably at least 5 carbon atoms.

Preferred variables for X, Y', Y" and n are as defined above in relation to formula (I).

Compounds of formula (VII), (VIIA) and (VIIB) may be prepared by conventional methods, for example by methods analogous to those described above in relation to formula (I). These novel compounds have liquid crystal properties and therefore their use in liquid crystal devices, either alone or in admixture with other liquid crystal compounds forms a further aspect of the invention.

The invention will now be particularly described by way of example.

EXAMPLE 1

Preparation of trans, trans-4'-(2-methoxyethoxy)-4-pentylbicyclohexane (Compound No. 2 in Table 1)

A solution of trans-4-(4-pentylcyclohexyl)-1-cyclohexanol (1.00 g, $3.97 \times 10^{-3}$ mol) in terahydrofuran (10 cm$^3$) was added dropwise to a suspension of sodium hydride (0.14 g, $5.95 \times 10^{-3}$ mol) in terahydrofuran (15 cm$^3$) at room temperature and under a nitrogen atmosphere. The solution was then left to stir (2 hrs) before 1-bromo-2-methoxyethane (0.83 g, $5.95 \times 10^{-3}$ mol) and potassium iodide (0.07 g, $3.97 \times 10^{-4}$ mol) were added dropwise and the reaction mixture then refluxed (48 hrs). Methanol (20 cm$^3$) was then added to the reaction mixture followed by water (75 cm$^3$). The product was then extracted into ether (3×30 cm$^3$) and then the combined organic layers were washed with brine (2×20 cm$^3$) and dried over magnesium sulphate. The solution was then filtered and the solvent removed under reduced pressure and the crude product purified by column chromatography on silica gel using a 3:7 ethylacetate/hexane mixture as eluent and recrystalised from cold propanone, producing the desired white crystalline product.

Yield 0.44 g (36%) GC purity (99.9%). Cr—I=65° C. $S_B$—I=64° C.

EXAMPLE 2

Using analogous methods to that described in Example 1 but with different starting materials, the following compounds were prepared.

trans, trans-4'-(2-ethoxyethoxy)-4-pentylbicyclohexane (Compound 4 in Table 1)

Yield 0.43 g (33%) GC purity (99.8%). Cr—I=25° C.

trans, trans-4'-(2-methoxyethoxy)-4-propylbicyclohexane (Compound 1in Table 1)

Yield 0.29 g (22%) GC purity (100%). Cr—I=47° C. N—I=44° C.

trans, trans-4'-(2-ethoxyethoxy)-4-propylbicyclohexane (Compound 3 in Table 1)

Yield 0.15 g (11%) GC purity (99.6%). Cr—I=20° C. N—I=7° C.

trans, trans-4'-(2-propoxyethoxy)-4-propylbicyclohexane (Compound 5 in Table 1)

Yield 0.08 g (12%) GC purity (100%). Cr—I=90° C.

EXAMPLE 3

Liquid Crystal Properties

The liquid crystal properties of the compounds of the invention were tested using conventional methods. In particular the melting and clearing points of compounds of the invention and structurally similar compounds were determined for comparison purposes. The results are shown in Tables 2–6.

Table 2 shows for the trans, trans-4-propyl,4'-R-bicyclohexyl core compound the effect of the position and number of oxygen atoms incorporated in the 5 atom end chain. All members of the series except the ethyleneoxy derivative exhibit a smectic B phase. Trans, trans-4-propyl,4'-pentylbicyclohexane shows only a smectic B phase. This is also the behaviour when one of the carbons in the pentyl chain is replaced with an oxygen. When, however, two carbons are replaced as in the methyl ethyleneoxy derivative Compound No 1, the smectic B phase is lost and a monotropic nematic phase is observed.

Table 3 shows for both the propyl and pentyl cyclohexyl analogues the effect of extending the ethyleneoxy chain by 1 carbon unit at the terminus. Extending the terminal chain by only 1 carbon atom has a very large effect on the melting point, which is substantially reduced in the C3 and C5 homologues Compounds 3 and 4 when compared with the shorter chain of Compounds 1 and 2.

TABLE 2

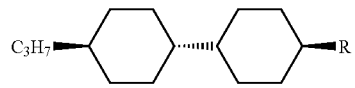

| Compound No. | R | Cr | SmB | N | Iso Liq |
|---|---|---|---|---|---|
| Comparative Example A | ⎯⎯⎯⎯ | • 23 | • 96 | — | • |
| Comparative Example B | ⎯O⎯⎯ | • 32 | • 74 | — | • |
| Comparative Example C | ⎯⎯O⎯ | • 15 | • 42 | — | • |

TABLE 2-continued

C₃H₇—[cyclohexyl]—[cyclohexyl]—R

| Compound No. | R | Cr | | SmB | | N | | Iso Liq |
|---|---|---|---|---|---|---|---|---|
| Comparative Example D | —CH₂—O— | • | 25 | • | 85 | — | | • |
| Compound no 1 | —O—CH₂CH₂—O— | • | 47 | | | (• 44) | | • |

TABLE 3

| Compound No. (Table 1) | Cr | | SmB | | N | | Iso Liq |
|---|---|---|---|---|---|---|---|
| 1 | • | 47 | • | | (• 44) | | • |
| 3 | • | 20 | • | | (• 7) | | • |
| 2 | • | 65 | (•64) | | | | • |
| 4 | • | 25 | | | | | • |
| 5 | • | 90 | | | | | • |

Table 4 shows the effect of the ethyleneoxy end chain with a number of different cores. Replacement of the cyclohexyl group with a phenyl group in Comparative Example 1A leads to a reduction in the stability of the nematic phase, which remains a monotropic transition, as it does in the tolane. A nematic phase is not observed in the biphenyl derivative.

TABLE 4

| Compound No. | Structure | Cr | | N | | Iso Liq |
|---|---|---|---|---|---|---|
| Compound No 1 | C₃H₇—[cyclohexyl]—[cyclohexyl]—O—CH₂CH₂—O— | • | 47 | • | (44) | • |
| Comparative Example 1A | C₃H₇—[cyclohexyl]—[phenyl]—O—CH₂CH₂—O— | • | 41 | • | (13) | • |
| Comparative Example 1B | C₃H₇—[phenyl]—[phenyl]—O—CH₂CH₂—O— | • | 97 | | | • |

A similar trend in melting and clearing points was found in the pentyl derivatives.

Table 5 shows the same cores and end chain as Table 4 but here the ethyleneoxy chain is extended by 1 carbon unit, to terminate in an ethyl group instead of a methyl group. The overall trends are again dependant on the core, the melting points are however reduced. None of the compounds exhibit an enantiotropic nematic phase.

TABLE 5

| Compound No. | Structure | Cr | | N | | Iso Liq |
|---|---|---|---|---|---|---|
| 3 | C₃H₇—[cyclohexyl]—[cyclohexyl]—O—CH₂CH₂—O—C₂H₅ | • | 20 | • | (7) | • |
| Comparative Example 3 | C₃H₇—[cyclohexyl]—[phenyl]—O—CH₂CH₂—O—C₂H₅ | • | 13 | • | (<−20) | • |

Table 6, the ethyleneoxy end chain is sequentially increased by 1 carbon unit from methyloxy- to propyloxy-ethenyloxy-bicyclohexyl. The melting point falls and then rises substantially in a typical manner as the end chain is increased in length.

TABLE 6

| Compound No. (Table 1) | Cr | N | Iso Liq |
|---|---|---|---|
| 1 | • | 47 | • (44) | • |
| 3 | • | 20 | • (7) | • |
| 5 | • | 90 | | • |

EXAMPLE 4

Physical Properties

The physical properties of a number of the compounds described were evaluated using conventional methods.

The dipole moments of the two compounds Comparative Example 2 and Compound No 2 were determined from extrapolation in solution in PCH32 at 25° C. at 4, 6, 8 and 10% concentrations measured in a 9 μm cell. The dipole moments for the two compounds appear very similar and are shown in Table 7.

TABLE 7

| Compound No. | Structure | μ(D) |
|---|---|---|
| Comparative Example 2 | 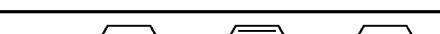 | 2.32 |
| Compound No 2 | 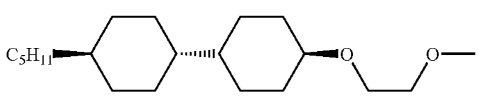 | 2.26 |

EXAMPLE 5

Properties of Mixtures

Mixtures of dicyclohexyl ethyleneoxy compounds in a standard basic mixture ethyl linked phenyl cyclohexanes were made and the phase behaviour, permittivities and birefringence determined. The mixtures, phase behaviour and structure of the compounds is listed in Table 8. None of the mixtures exhibited higher order smectic phases.

The permittivities of the mixtures are shown in Table 9.

TABLE 9

| Mixture | ε∥ | ε⊥ | Δε |
|---|---|---|---|
| I | 11.8684 | 5.1236 | 6.75 |
| II | 11.6578 | 5.1522 | 6.51 |
| Mixture ethyl linked phenyl cyclohexanes | 12.95 | 5.13 | 7.82 |

The birefringence of the mixtures of 25° C. and 30° below the clearing point of the mixture are given in Table 10. All mixtures show low birefringence.

TABLE 10

| Mixture | Temperature (° C.) | $n_e$ | $n_o$ | Δn |
|---|---|---|---|---|
| I | 25 | 1.5713 | 1.4833 | 0.088 |
| | 19.9 | 1.5755 | 1.4841 | 0.091 |
| II | 25 | 1.5683 | 1.4841 | 0.084 |
| | 16.5 | 1.5750 | 1.4853 | 0.0897 |

The invention claimed is:

1. A method for increasing the u.v. stability of a liquid crystal mixture comprising adding to or including in a liquid crystal mixture a compound of formula (I)

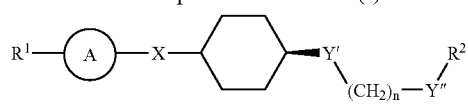

(I)

TABLE 8

| Mixture number, % of compound | Compound No and transition temperatures | Structure | Clearing point of mixture (° C.) |
|---|---|---|---|
| I 9.75% | 2 K65(SmB 64) | 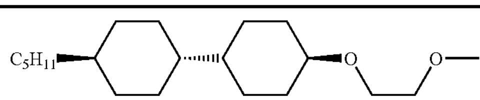 | 49.9 |
| II 9.94% | 4 K27.2I |  | 46.5 | wherein R¹ is an alkyl or alkenyl group, either of which may be optionally interposed with one or more oxygen or sulphur atoms, R² is an alkyl or alkenyl group, Y' and Y" are independently selected from oxygen or sulphur, n is an integer from 1 to 5, X is a direct bond or a $C_{1-4}$alkylene or $C_{2-4}$alkenylene chain, and A is group comprising one or two rings which are independently selected from aryl or heterocyclic rings, and when there are two rings, they are bonded together directly or by way of a $C_{1-4}$alkylene or $C_{2-4}$alkenylene group.

2. The method according to claim 1 wherein the group A in formula (I) is selected from a group of formula (i), (ii), (iii), (iv) or (v)

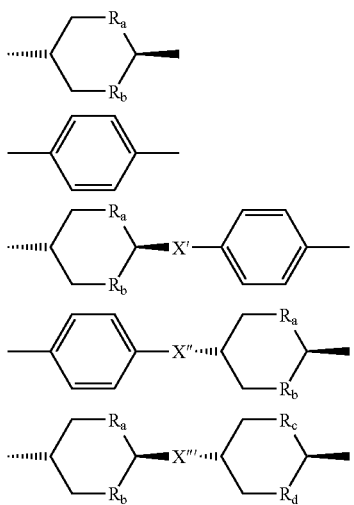

where X', X" and X'" are each selected from a direct bond, a $C_{1-4}$alkylene chain or a $C_{2-4}$alkenylene chain, and groups $R_a$, $R_b$, $R_c$ and $R_d$ are oxygen.

3. The method according to claim 1 wherein Y' and Y" in formula (I) are oxygen.

4. The method according to claim 1 wherein n in formula (I) is 2.

5. The method according to claim 1 wherein R² in formula (I) is a $C_{1-10}$alkyl.

6. The method according to claim 5 wherein R² in formula (I) is $C_{1-3}$alkyl.

7. The method according to claim 1 wherein X in formula (I) is a direct bond or a $C_{1-2}$alkylene chain.

8. The method according to claim 7 wherein X in formula (I) is a direct bond.

9. The method according to claim 1 wherein X is a $C_{2-4}$alkenylene chain of formula (x), (xi) or (xii)

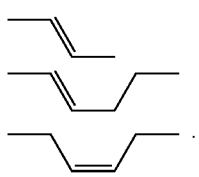

10. The method according to claim 1 wherein the compound of formula (I) is a compound of formula (IA)

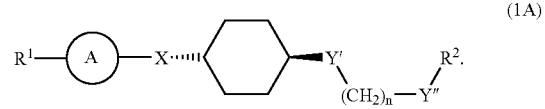

11. The method according to claim 1 wherein R¹ in formula (I) is a straight chain $C_{1-6}$alkyl group which optionally contains one or two oxygen or sulphur atoms.

12. The method according to claim 1 wherein R¹ in formula (I) is a $C_{2-10}$alkenyl group.

13. The method according to claim 12 wherein the alkenyl group R¹ contains two double bonds.

14. The method according to claim 13 wherein the alkenyl group R¹ is a diene of formula (VI)

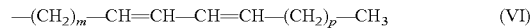

where m and p are 0 or an integer from 1–5, provided that m+p does not exceed 5.

15. A compound of claim 1

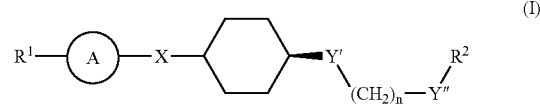

wherein R¹ an alkyl or alkenyl group, either of which may be optionally interposed with one or more oxygen or sulphur atoms, R² is an alkyl or alkenyl group, Y' and Y" are independently selected from oxygen or sulphur, n is an integer from 1 to 5, X is a direct bond or a $C_{1-4}$alkylene or a $C_{2-4}$alkenylene chain, and A is group comprising one or two rings which are independently selected from aryl or heterocylic rings, and when there are two rings, they are bonded together directly or by way of a $C_{1-4}$alkylene or $C_{2-4}$alkenylene group.

16. A liquid crystal device comprising an outdoor liquid crystal display device, or a device comprising a phosphorescent substrate or a phosphor layer, said device comprising a compound of formula (I) as defined in claim 15.

17. A liquid crystal device according to claim 16 wherein the compound of formula (I) is in admixture with other liquid crystal compounds.

18. A liquid crystal device which comprises a display cell comprising a layer of a liquid crystal material wherein the liquid crystal material comprises a compound of formula (I) as defined in claim 15, means for addressing the liquid crystal material so as to allow light to pass through it when appropriately addressed, and an emitting layer comprising phosphor elements, arranged to receive light passing through the liquid crystal layer.

19. A method for preparing a compound of formula (I), which compound is as defined in claim 15, which method comprises reacting a compound of formula (IV)

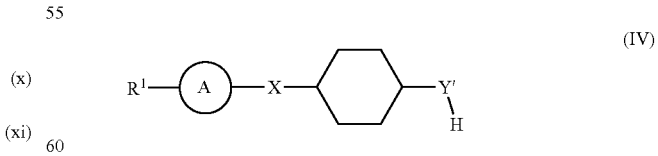

with a compound of formula (V)

where Z is a leaving group, so as to form a compound of claim 15.

* * * * *